(12) United States Patent
Turkbas (10) Patent No.: US 10,661,062 B2
(45) Date of Patent: May 26, 2020

(54) MOUTHGUARD WITH SELECTIVE FLAVOR COMPONENTS

(71) Applicant: Shock Doctor, Inc., Fountain Valley, CA (US)

(72) Inventor: Jay Turkbas, Orono, MN (US)

(73) Assignee: Shock Doctor, Inc., Fountain Valley, CA (US)

( * ) Notice: Subject to any disclaimer, the term of this patent is extended or adjusted under 35 U.S.C. 154(b) by 247 days.

(21) Appl. No.: 14/191,149

(22) Filed: Feb. 26, 2014

(65) Prior Publication Data

US 2014/0238418 A1 Aug. 28, 2014

Related U.S. Application Data

(60) Provisional application No. 61/769,384, filed on Feb. 26, 2013, provisional application No. 61/769,382, filed on Feb. 26, 2013.

(51) Int. Cl.
*A61M 31/00* (2006.01)
*A61C 19/06* (2006.01)
*A63B 71/08* (2006.01)

(52) U.S. Cl.
CPC ......... *A61M 31/002* (2013.01); *A61C 19/063* (2013.01); *A63B 71/085* (2013.01); *A63B 2213/00* (2013.01)

(58) Field of Classification Search
CPC .... A61F 5/566; A61F 5/56–58; A63B 71/085; A63B 2071/008; A63B 2071/086; A63B 71/08–10; A61C 7/08; A61C 19/063–066; A61C 9/00–0013; A61M 16/0488–0497
USPC .................. 128/861, 862; 433/6, 7
See application file for complete search history.

(56) References Cited

U.S. PATENT DOCUMENTS

| | | | |
|---|---|---|---|
| 1,146,264 | A | 7/1915 | Kelly |
| 2,444,294 | A | 6/1948 | Jones et al. |
| 2,521,039 | A | 9/1950 | Carpenter |
| 2,827,899 | A | 3/1958 | Altieri |
| 3,089,487 | A | 5/1963 | Enicks et al. |
| 3,103,217 | A | 9/1963 | Butler et al. |
| 3,333,582 | A | 8/1967 | Cathcart |
| D212,848 | S | 12/1968 | Westlund |

(Continued)

FOREIGN PATENT DOCUMENTS

| | | |
|---|---|---|
| GB | 2491183 A | 11/2012 |
| WO | 2014093850 A1 | 6/2014 |

OTHER PUBLICATIONS

International Search Report and Written Opinion issued in PCT/US2014/018755, dated May 22, 2014, 8 pages.

(Continued)

*Primary Examiner* — Alireza Nia
*Assistant Examiner* — Michelle J Lee
(74) *Attorney, Agent, or Firm* — Faegre Drinker Biddle & Reath LLP (57) ABSTRACT

A composite flavored mouthguard comprising a mouthguard base including a first material; an elastomeric frame including a second material; and a liner including a third material, wherein at least one of the first material, the second material, or the third material includes a flavorant and at least one of the first material, the second material, or the third material independently includes a flavorant that provides sweetness.

23 Claims, 12 Drawing Sheets

(56) References Cited

U.S. PATENT DOCUMENTS

| | | | |
|---|---|---|---|
| 3,505,995 A | 4/1970 | Greenberg | |
| 3,768,465 A | 10/1973 | Helmer | |
| 3,788,314 A | 1/1974 | Noreen | |
| RE28,667 E | 12/1975 | Gores | |
| 4,134,400 A | 1/1979 | DiMatteo | |
| 4,495,945 A | 1/1985 | Liegner | |
| 4,568,280 A | 2/1986 | Ahlin | |
| 4,977,905 A | 12/1990 | Kittelsen et al. | |
| 5,031,638 A * | 7/1991 | Castaldi | A63B 71/085 |
| | | | 128/861 |
| 5,063,940 A | 11/1991 | Adell et al. | |
| 5,117,816 A | 6/1992 | Shapiro et al. | |
| D328,494 S | 8/1992 | Schwendeman et al. | |
| D328,965 S | 9/1992 | Ewing | |
| 5,165,424 A | 11/1992 | Silverman | |
| 5,277,203 A | 1/1994 | Hays | |
| 5,293,880 A | 3/1994 | Levitt | |
| 5,339,832 A * | 8/1994 | Kittelsen | A61C 5/00 |
| | | | 128/859 |
| 5,406,963 A * | 4/1995 | Adell | A61C 9/0006 |
| | | | 128/861 |
| 5,566,683 A | 10/1996 | Thornton | |
| 5,642,737 A | 7/1997 | Parks | |
| D382,965 S | 8/1997 | Wagner | |
| 5,692,523 A | 12/1997 | Croll et al. | |
| 5,826,581 A * | 10/1998 | Yoshida | A63B 71/085 |
| | | | 128/859 |
| 5,842,860 A | 12/1998 | Funt | |
| 5,970,981 A | 10/1999 | Ochel | |
| 6,036,487 A | 3/2000 | Westerman | |
| 6,068,475 A | 5/2000 | Stoyka, Jr. | |
| 6,082,363 A * | 7/2000 | Washburn | A63B 71/085 |
| | | | 128/859 |
| D452,011 S | 12/2001 | Redhage | |
| 6,405,729 B1 | 6/2002 | Thornton | |
| 6,584,978 B1 | 7/2003 | Brett et al. | |
| 6,691,710 B2 * | 2/2004 | Kittelsen | A63B 71/085 |
| | | | 128/859 |
| 6,978,786 B2 | 12/2005 | Sabbagh | |
| D530,863 S | 10/2006 | Manzo et al. | |
| D541,481 S | 4/2007 | Farrell | |
| 7,210,483 B1 | 5/2007 | Frank Lesniak et al. | |
| 7,216,371 B2 | 5/2007 | Wong | |
| 7,299,804 B2 | 11/2007 | Kittelsen et al. | |
| 7,658,193 B2 | 2/2010 | Lesniak | |
| D614,304 S | 4/2010 | Jansheski | |
| 7,757,310 B2 | 7/2010 | Wong | |
| D641,478 S | 7/2011 | Belvedere et al. | |
| 8,033,392 B1 | 10/2011 | Gehner et al. | |
| 8,116,854 B2 | 2/2012 | Hart et al. | |
| D663,485 S | 7/2012 | Turkbas et al. | |
| D663,486 S | 7/2012 | Turkbas et al. | |
| 8,235,052 B2 | 8/2012 | Maurello | |
| D688,832 S | 8/2013 | Polk, III | |
| 8,607,798 B2 | 12/2013 | Turkbas et al. | |
| 2003/0075184 A1 * | 4/2003 | Persichetti | A63B 71/085 |
| | | | 128/861 |
| 2003/0205234 A1 | 11/2003 | Bardach et al. | |
| 2007/0084471 A1 | 4/2007 | Napoli et al. | |
| 2007/0151567 A1 | 7/2007 | Maurello | |
| 2007/0151568 A1 * | 7/2007 | Maurello | A63B 71/085 |
| | | | 128/859 |
| 2007/0235039 A1 * | 10/2007 | Gottsch | A63B 71/085 |
| | | | 128/859 |
| 2009/0038624 A1 | 2/2009 | Akervall et al. | |
| 2010/0055233 A1 * | 3/2010 | Macinnis | C08J 3/226 |
| | | | 426/6 |
| 2010/0304338 A1 * | 12/2010 | Cramer | C08F 2/48 |
| | | | 433/202.1 |
| 2011/0114100 A1 | 5/2011 | Alvarez et al. | |
| 2011/0186055 A1 | 8/2011 | Makkar et al. | |
| 2011/0230587 A1 | 9/2011 | MacInnis et al. | |
| 2012/0017922 A1 | 1/2012 | Hirshberg | |
| 2012/0085354 A1 | 4/2012 | Polk, III | |
| 2012/0090625 A1 | 4/2012 | Evans et al. | |
| 2012/0111343 A1 | 5/2012 | Turkbas et al. | |
| 2013/0087157 A1 | 4/2013 | Hawkins | |
| 2013/0104913 A1 | 5/2013 | Evans et al. | |
| 2014/0090655 A1 * | 4/2014 | Robinson | A63B 71/085 |
| | | | 128/862 |
| 2014/0166024 A1 | 6/2014 | Davidson et al. | |
| 2014/0238417 A1 | 8/2014 | Turkbas | |
| 2014/0238418 A1 | 8/2014 | Turkbas | |
| 2014/0261465 A1 * | 9/2014 | Turkbas | A63B 71/085 |
| | | | 128/862 |

OTHER PUBLICATIONS

International Search Report and Written Opinion issued in PCT/US2014/018756, dated Jun. 3, 2014, 11 pages.

European Search Report issued in EP Application No. 14757382 dated Nov. 2, 2016, 9 pages.

Extended European Search Report issued in EP application No. 14756802.6, dated Oct. 31, 2016, 10 pages.

International Preliminary Report on Patentability issued in PCT/US2014/018755, dated Sep. 1, 2015, 5 pages.

International Preliminary Report on Patentability issued in PCT/US2014/018756, dated Sep. 11, 2015, 8 pages.

Shock Doctor Gel Max Mouthguard, www.shockdoctor.com/gel-max-mouthguard, accessed Jan. 24, 2017, at least available on Apr. 10, 2016.

Shock Doctor SuperFit Mouthguard, www.shockdoctor.com/superfit-mouthguard, accessed Jan. 24, 2017, at least available on Apr. 10, 2016.

Shock Doctor Ultra Double Braces Mouthguard, www.shockdoctor.com/ultra-double-braces-mouthguard, accessed Jan. 24, 2017, at least available on Apr. 10, 2016.

Shock Doctor Ultra2 SIC Mouthguard, www.shockdoctor.com/ultra2-stc-mouthguard, accessed Jan. 24, 2017, at least available on Apr. 10, 2016.

* cited by examiner

MOUTHGUARD WITH SELECTIVE FLAVOR COMPONENTS

CROSS-REFERENCE TO RELATED APPLICATION

This application claims priority to Provisional Application No. 61/769,384, filed Feb. 26, 2013 and entitled, "MOUTHGUARD WITH FLAVOR INSERTS," and Provisional Application No. 61/769,382, filed Feb. 26, 2013, and entitled, "MOUTHGUARD WITH SELECTIVE FLAVOR COMPONENTS," the contents of which are herein incorporated by reference in their entirety.

BACKGROUND

Mouthguards are often used to protect the teeth, oral tissue and gums from impact and abrasion. Different types of mouthguards are available including non-personalized and those that are custom formed to the teeth of an individual user.

SUMMARY

Aspects of various embodiments relate to a mouthguard that is configured to encourage its continued use by including one or more flavoring components. The one or more flavoring components can provide a variety of different tastes and scents, including sweetness. In some embodiments, the invention relates to a composite flavored mouthguard including a mouthguard base having a generally U-shaped profile forming an upper channel, the mouthguard base including a first material, an elastomeric frame disposed at least partially within the mouthguard base, the elastomeric frame including a second material and a liner disposed within the upper channel, the liner including a third material. At least one of the first material, the second material, and the third material independently includes one or more flavorants or other additive. In some embodiments, the one or more flavorants can include a flavorant that provides sweetness.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

In some embodiments, a composite mouthguard is formed of several different polymeric materials. At least one of the polymeric materials can include one or more flavorants. In some embodiments, at least one of the one or more flavorants can include a sweetener. In some embodiments, individual flavorants are in different polymeric materials, with the polymeric materials defining different mouthguard layers as desired. In some embodiments, at least one of the polymeric materials can include two or more distinct flavorants, with one of the flavorants being a sweetener. In some embodiments, at least one of the polymeric materials can be free of flavorants.

Flavors are generally defined as the sensory impression provided to the person detecting the flavor. The flavor detected by an individual can be a combination of taste and smell. Examples of tastes include sweet, sour, bitter, salty and other basic tastes. Smells are limitless. Flavorants are substances that provide a flavor or alter the detected flavor. Flavorants can be natural or synthetic. Salts are flavorants that enhance a salty taste. Sugars and other sweeteners are flavorants that enhance a sweet taste.

Illustrative but non-limiting examples of flavors, or taste components, that can be used in the flavored mouthguards described herein include a sweet flavor, a tart flavor, a salty flavor, a citrus flavor such as orange or lemon, a berry flavor such as strawberry, a mint flavor such as peppermint, spearmint, and the like. Other flavorants include cinnamon. It will be appreciated that flavorants can be combined in order to provide additional taste combinations. Two or more flavorants can be combined into a single polymer layer, or the flavorants can be separated, one in each polymer layer. In some embodiments, flavorants are disposed in separate layers to be deployed in targeted areas of the mouth. For example, a flavorant that is sweet, such as sucralose, is optionally deployed in layer toward a front region of the mouth while a different type of flavorant, such as a citrus flavorant, is optionally deployed in layer toward a back region of the mouth.

A variety of flavorants can be used, including GRAS (generally regarded as safe) natural and artificial flavorants. In some embodiments, particular flavorants can be selected not only to provide a desired flavor or aroma, but also to accommodate the thermal processing parameters involved in molding a particular polymer. Some flavorants are disposed within water soluble carriers or oil soluble carriers. It will be appreciated that in some instances, a flavorant in an oil soluble carrier may have an increased affinity for the polymer to which the flavorant is added.

In some embodiments, the flavorants include one or more flavorants that can provide a sweet taste, or sweetness. A variety of different sweeteners can be used, including GRAS natural and artificial sweeteners. The sweetness-providing flavorants can be selected not only to provide a desired sweetness, but also in accordance with the thermal processing parameters of the polymer to which the sweetener is to be added.

Illustrative but non-limiting examples of suitable sweeteners include sugar alcohols such as sorbitol, maltitol, xylitol, mannitol, erythritol, and lactitol. Additional suitable sweeteners include saccharin, sucralose, and extracts from the Stevia plant. The sweetener can be added in any desired concentration and can be added to the polymer in any suitable form, such as a liquid or a powder that can be mixed into a liquid polymer prior to molding. In some embodiments, the sweetener can be added at a concentration of about 0.5 to about 20 weight percent of the polymer. It will be appreciated that the desired concentration level can vary, depending on the particular sweetener being used, the desired taste effect, and the specific polymer to which the sweetener is being added.

The flavorant can be added in any desired concentration. In some embodiments, flavorants providing tastes other than sweet can be added at a concentration of about 3 to about 30 weight percent of the polymer. In some embodiments, flavorants providing sweetness can be added at a concentration of about 0.5 to about 20 weight percent of the polymer. It will be appreciated that the desired concentration level can vary, depending on the particular flavorant being used, the desired taste effect, and the specific polymer the flavorant is being added to. In some embodiments, the flavorant can be added to the polymer when making a master batch pellet that can subsequently be used when molding the mouthguard 200.

In some embodiments, the flavorants such as flavor oils or powders can be mixed into a container of pellets that do not already include any flavorants. As a result of mixing, the pellets become coated with the flavorants and at least some of the flavorants can absorb into the pellets. The pellets are added to the injection molding machine in which friction and pressure melts and blends the material as it flows through the injection molding machine.

Figure 1:
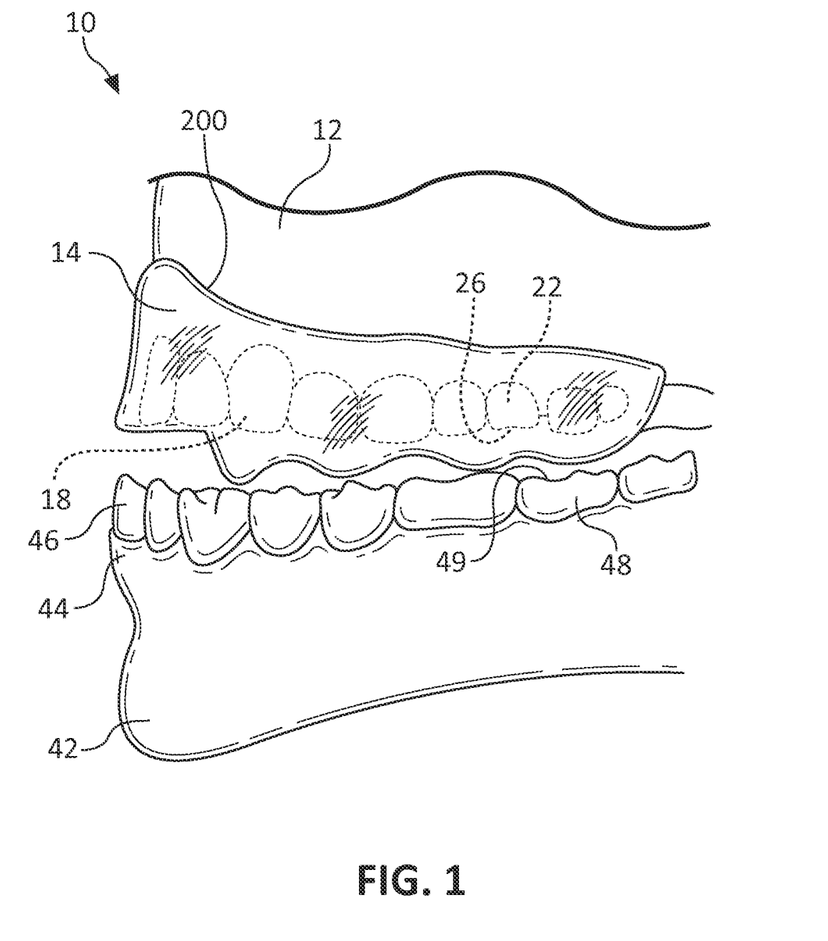
FIG. 1 is a partial elevational view showing the jaws and mouth of a user wearing a mouthguard, according to some embodiments.

Turning to the Figures, FIG. 1 illustrates the environment in which a mouthguard 200 is used. A mouthguard user has a mouth 10, generally including a rigid upper jaw 12 and a movable lower jaw 42 which are movably coupled at a temporomandibular joint (TMJ). The rigid upper jaw 12 has gum tissue 14 within mouth 10. Gum tissue 14, as well as the bone thereunder, support anterior teeth (incisors and canines) 18 which have incisal or biting surfaces. The gum tissue 14 and the bone thereunder also support posterior teeth (molars and bicuspids) 22 which have cusps and biting surfaces 26. The movable lower jaw 42 supports a bone covered by gum tissue 44 which further supports anterior teeth (incisors and canines) 46 and posterior teeth (molars and bicuspids) 48 with occlusal surfaces 49.

FIGS. 2 through 8 provide illustrative but non-limiting views of the components that together form the illustrative mouthguard 200. In some embodiments, as illustrated, the mouthguard 200 is formed a step at a time, as subsequent polymeric layers or structures are combined. Generally, the mouthguard 200 includes a mouthguard base 300 formed of a first material, an elastomeric frame 400 formed of a second material, and a liner 500 formed of a third material. While the mouthguard base 300 is described as being formed of a first material, the elastomeric frame 400 is described as being formed of a second material and the liner 500 is described as being formed of a third material, it will be appreciated that first, second and third merely denote materials, and do not necessarily denote the order in which the mouthguard 200 is formed, or the order in which the individual layers are formed or combined.

In some embodiments, a mouthguard may only be formed of two materials, such as an outer frame formed of a first material and an inner gel that is disposed within the outer frame. The outer frame can include a flavorant and the inner gel can include a flavorant that provides sweetness. In some embodiments, the inner gel can include two or more flavorants, including a flavorant that provides sweetness. In some embodiments, the outer frame can include two or more flavorants, including a flavorant that provides sweetness. In some embodiments, the outer frame can include a flavorant providing sweetness and the inner gel can include a flavorant that provides a particular flavor.

In some embodiments, the mouthguard 200 can be considered as being a "boil and bite" mouthguard 200. Before use of the mouthguard 200, a user must fit the mouthguard 200 in their mouth. To do this, the mouthguard 200 is momentarily submersed into boiling water for 16-60 seconds. This will cause the liner 500 to soften without appreciably softening the mouthguard base 300. Thereafter, the mouthguard apparatus 200 is immediately placed onto the teeth 18 and 22 of the upper jaw 12 (FIG. 1). The U-shaped mouthguard base 300 will cover the posterior teeth of the upper jaw up, including the third molar. The user bites down firmly and applies suction between the upper jaw 12 and the mouthguard 200 while packing the mouthguard 200 with the hands along the cheeks and gums adjacent the anterior and posterior teeth 18 and 22 of the upper jaw 12 (FIG. 1). The posterior teeth 48 of the lower jaw 42 will properly index upon the bottom surface of the mouthguard base 300.

The third material of the liner 500 softens at a temperature in the range of about 100 to about 150 degrees Fahrenheit, and the first material of the mouthguard base 300 softens at a temperature that is in the range of about 140 to about 200 degrees Fahrenheit. When the mouthguard 200 is placed in the boiling water, the liner 500 will become softer than the mouthguard base 300. The liner 500 will easily conform to all of the contours of the teeth while the mouthguard base 300 is not appreciably deformed, except to conform somewhat to the outer dimensions of the teeth and gums. The fitting process causes displacement of the liner 500 around the individual teeth, allowing the liner to conform to the exact tooth shape, unlike standard mouthguards which only conform to the outside of the teeth. Since the third material is in the form of a liner 500 rather than filling the U-shaped base, the amount of third material that squirts out is kept to a minimum. As the mouthguard 200 cools, the liner 500 remains softer than the mouthguard base 300, retains the fit of the user's teeth. Because of this close fit, the mouthguard 200 will be retained and the wearer will have fewer tendencies to chew on it. Furthermore, as a user chews on the soft third material, the third material is less likely to crumble in a user's mouth.

Figure 2:
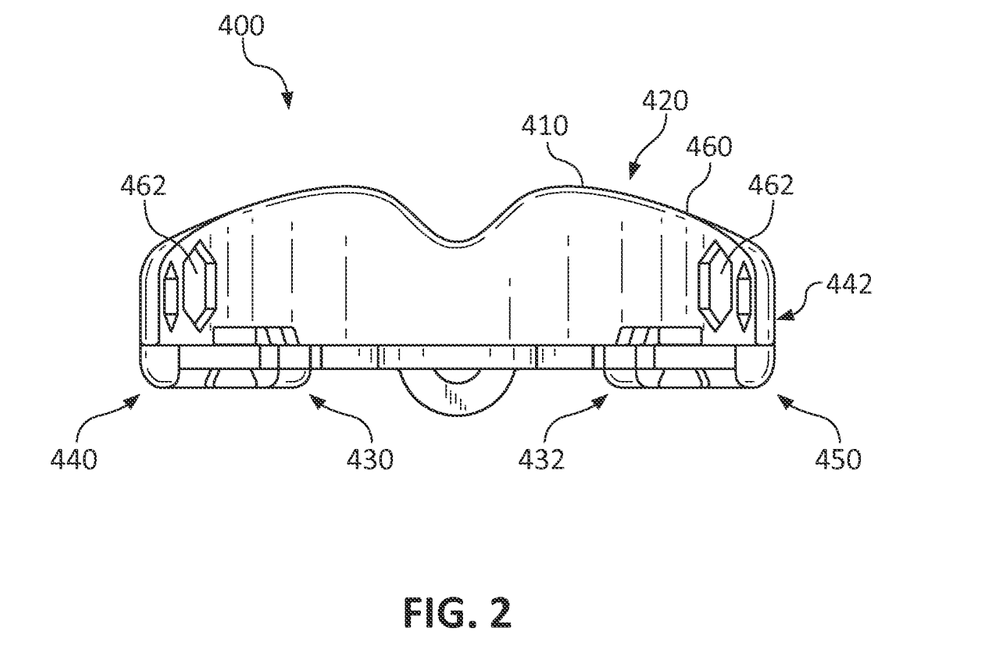
FIG. 2 is a posterior perspective of an elastomeric frame, according to some embodiments.
Figure 3:
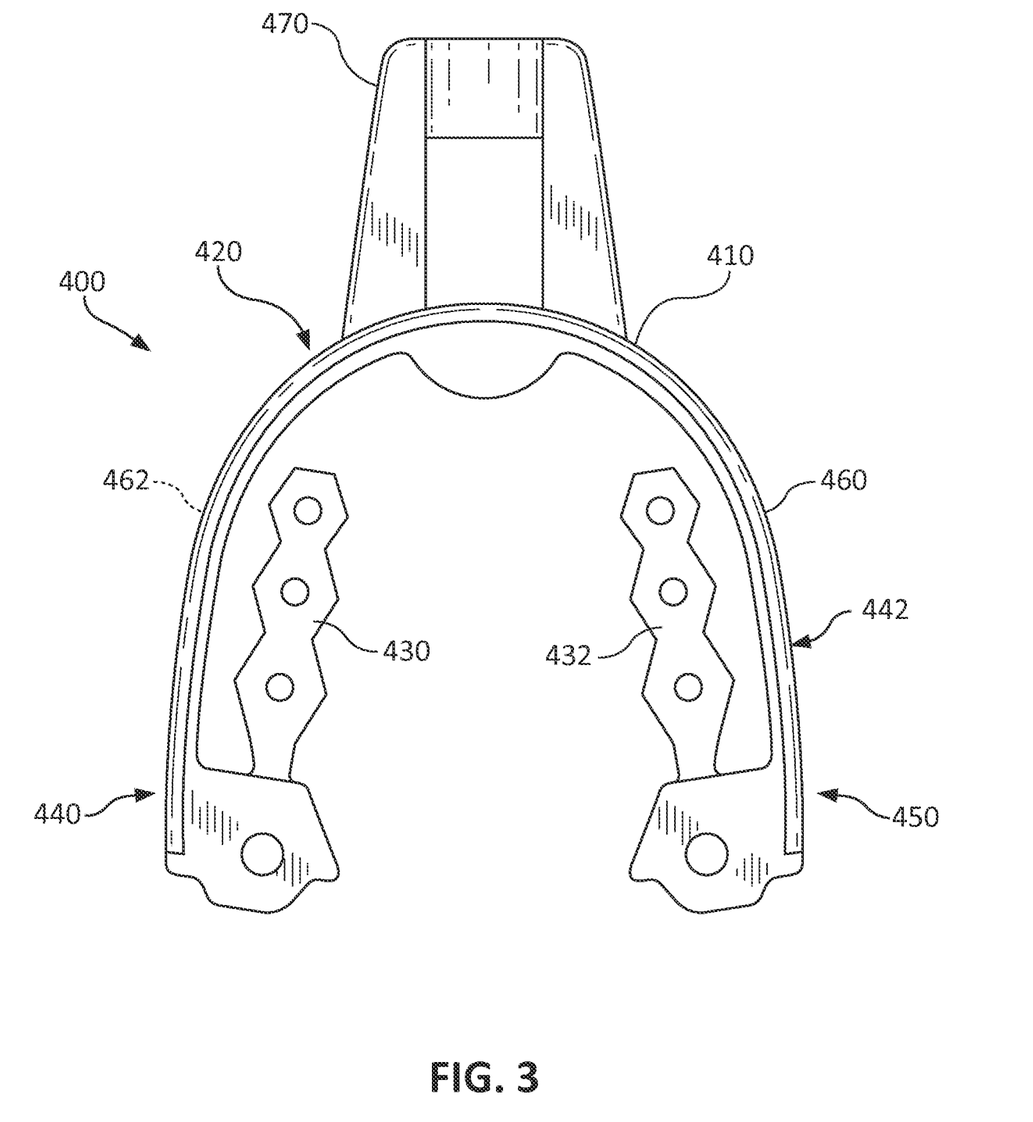
FIG. 3 is a raised perspective view of the elastomeric frame of FIG. 2, according to some embodiments.
Figure 4:
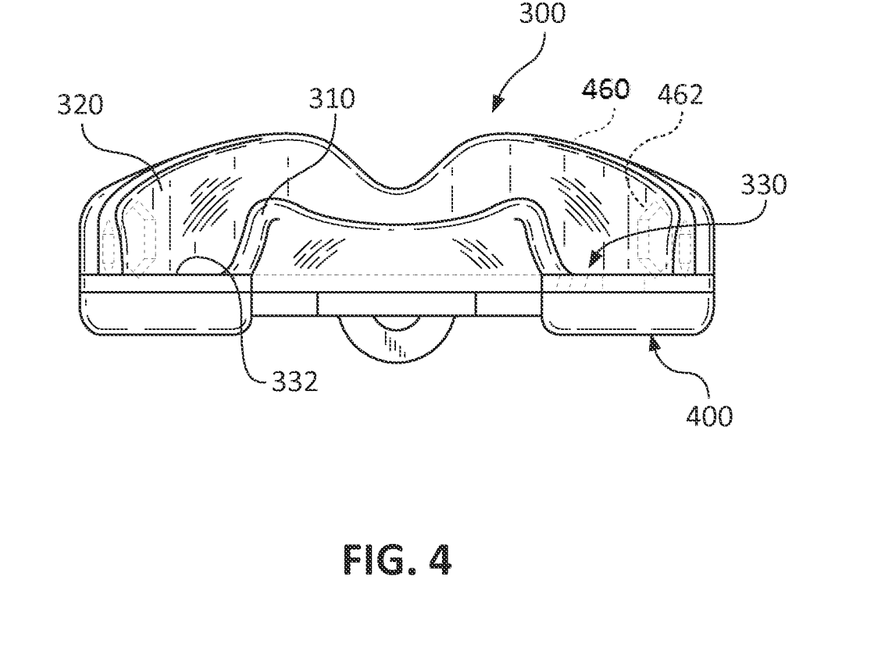
FIG. 4 is a posterior perspective view of the elastomeric frame of FIG. 2 in combination with a mouthguard base molded about the elastomeric frame, according to some embodiments.
Figure 5:
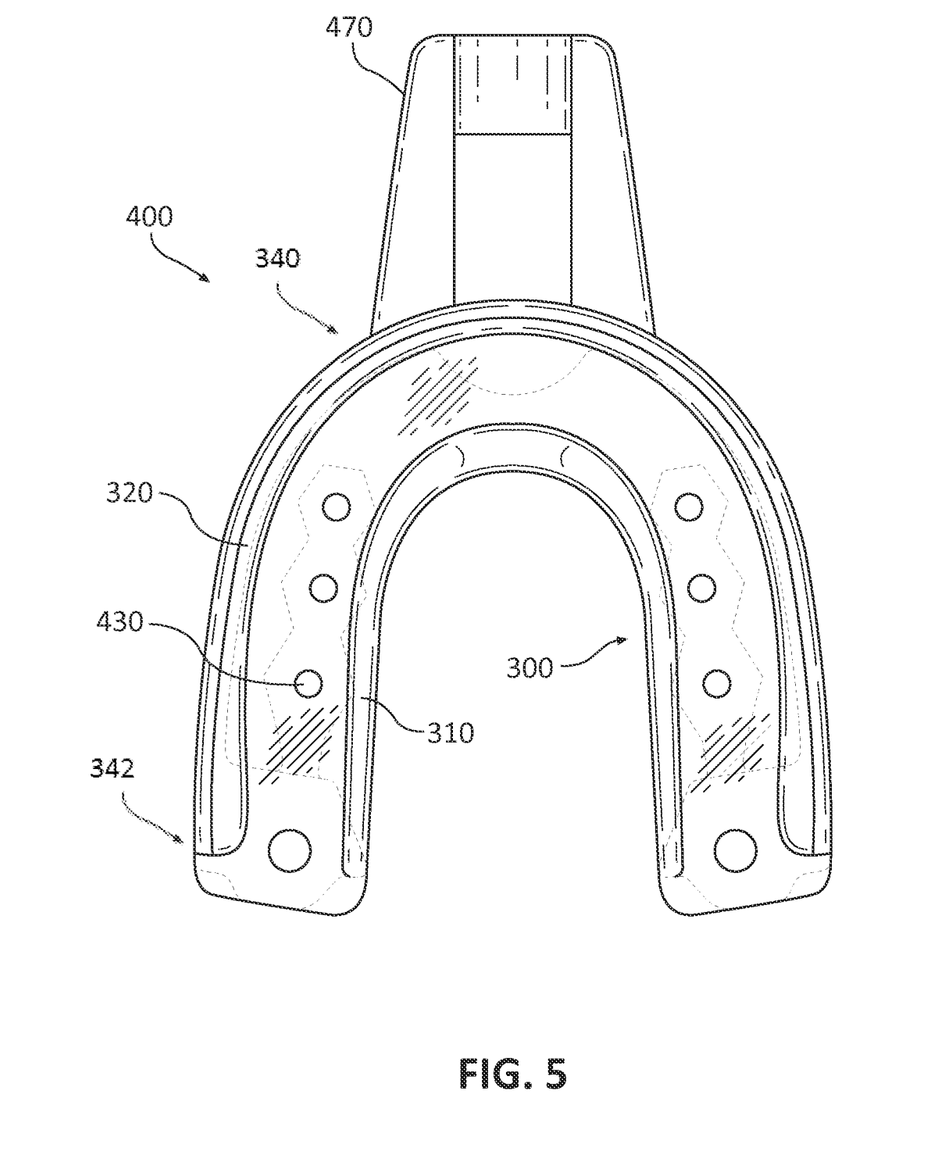
FIG. 5 is a raised perspective view of the combination of FIG. 4, according to some embodiments.
Figure 6:
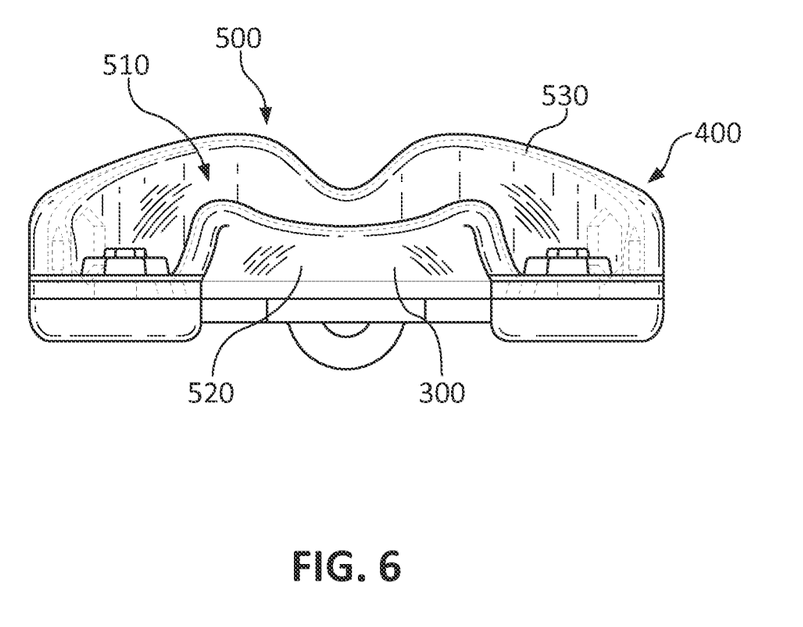
FIG. 6 is a posterior perspective view of a mouthguard including the elastomeric frame of FIG. 2, the mouthguard base of FIG. 4 and a liner, according to some embodiments.
Figure 7:
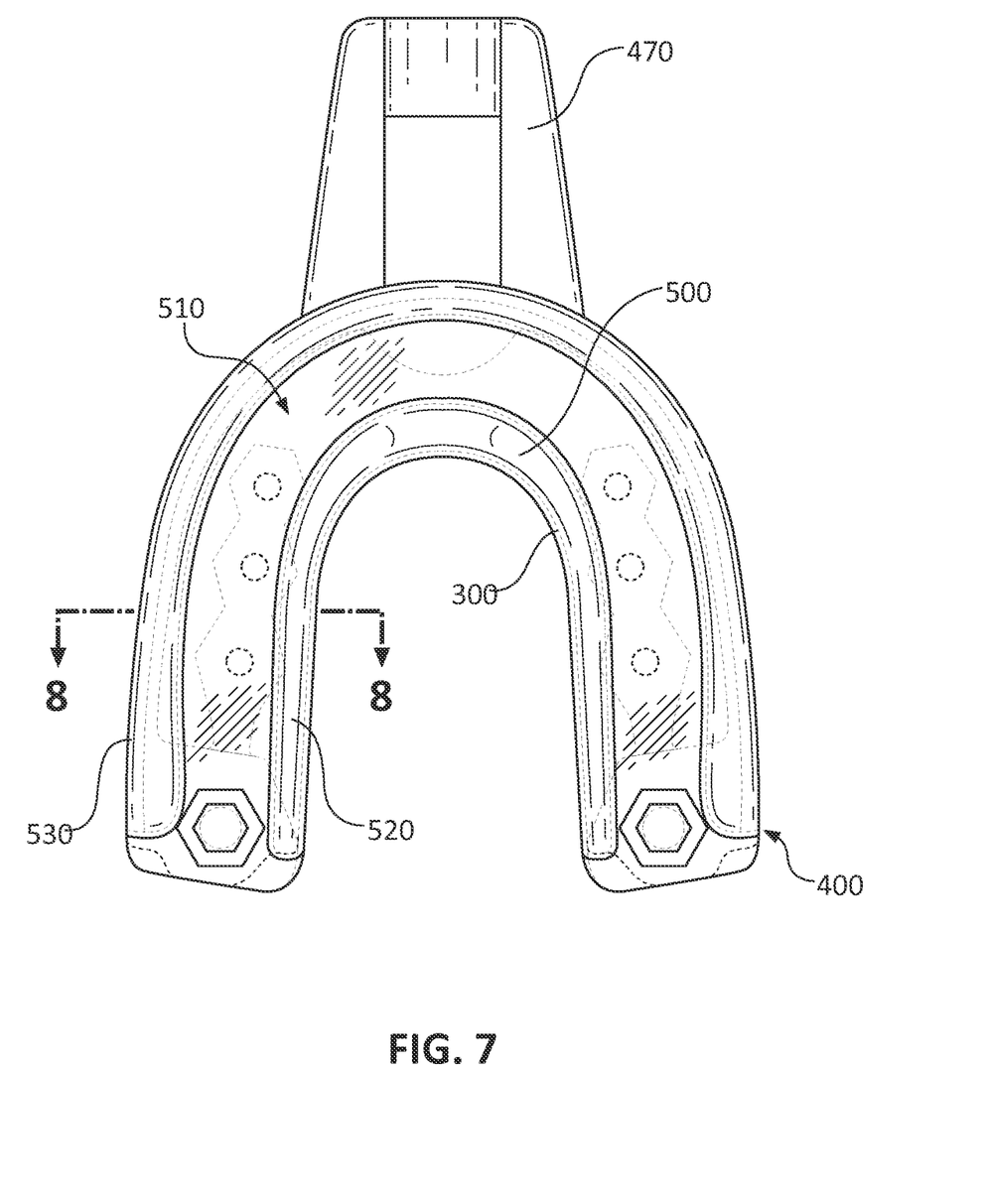
FIG. 7 is a raised perspective of the mouthguard of FIG. 6, according to some embodiments.
Figure 8:
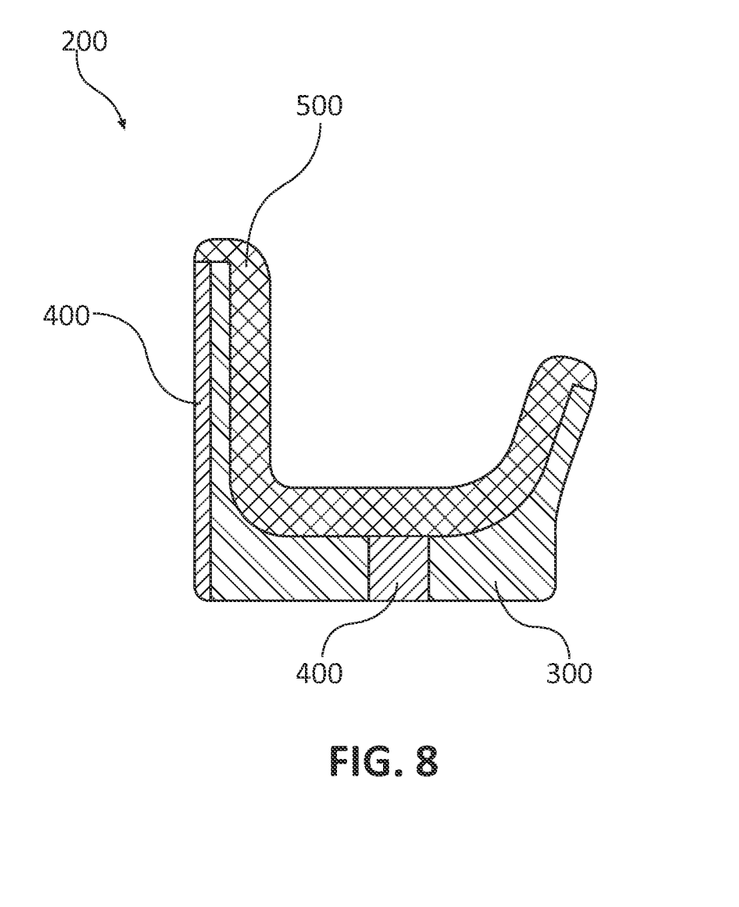
FIG. 8 is a cross-sectional view taken along line 8-8 of FIG. 7, according to some embodiments.

FIGS. 2 and 3 illustrate the elastomeric frame 400, FIGS. 4 and 5 illustrate the mouthguard base 300 in combination with the elastomeric frame 400, and FIGS. 6 through 8 illustrate the mouthguard base 300 in combination with the elastomeric frame 400 and the liner 500. In some embodiments, the mouthguard 200 can be formed by molding the mouthguard base 300 around a previously formed elastomeric frame 400, followed by molding the liner 500 onto the combination of the mouthguard base 300 and the elastomeric frame 400.

With reference to FIGS. 2 and 3, the elastomeric frame 400 includes an impact shield portion 410 that is located at an anterior portion 420 of the elastomeric frame 400. The elastomeric frame 400 also includes a first plurality of cushion pads 430 that extend from a first side 440 of a posterior portion 450 of the elastomeric frame 400 and a second plurality of cushion pads 432 that extend from a second side 442 of the elastomeric frame 400. It will be appreciated that the shape and pattern of the elastomeric frame 400 is illustrative only. In some embodiments, the cushion pads 430, 432 can have other patterns and shapes. In some embodiments, the cushion pads 430, 432 can be distinct from the impact shield portion 410. In some embodiments, the cushion pads 430, 432 help assure proper fitting of the mouthguard 200 when softened by preventing the user from biting too deeply into the materials forming the mouthguard base 300 and/or the liner 500. In some embodiments, the cushion pads 430, 432 are elastomeric, which means that they can deform and return to their original shape in order to help absorb energy when the mouthguard 200 is subjected to an impact force.

In some embodiments, as illustrated, the elastomeric frame 400 includes a wall portion 460 that forms the impact shield portion 410 and extends posteriorly along the first side 440 and the second side 442. In some embodiments, as illustrated, the cushion pads 430, 432 are spaced apart from the wall portion 460 in order to align the cushion pads 430, 432 within the mouthguard 200 such that the cushion pads 430, 432 align with the desired teeth. In some embodiments, as illustrated, the wall portion 460 includes a plurality of apertures 462. The apertures 462, if included, can contribute to the visual appearance of the mouthguard 200. In some embodiments, the apertures 462 can aid in securing together different portions of the mouthguard 200.

In some embodiments, the mouthguard 200 can be configured to include a tether that can be used by the player to attach the mouthguard 200 to a helmet. The tether can be permanently attached, or the tether can be removable and insertable by the player. As illustrated in FIG. 3, in some embodiments the elastomeric frame 400 includes a tether mouth 470 that extends from the anterior portion 420 of the mouthguard 200.

As noted, in some embodiments of the mouthguard 200, the elastomeric frame 400 is formed of a second material that can include one or more flavorants. In some embodiments, the one or more flavorants include a flavorant that provides sweetness. The second material can be a non-softening, resilient, low compression elastomer which, unlike copolymers of ethylene and vinyl acetate (i.e., EVA), exhibits a high resilience, low compression, shape maintenance, and shock absorption attenuation and dissipation. Virtually all rubbers that exhibit these physical characteristics may be used for the elastomeric frame 400, including vulcanized rubber.

In some embodiments, the second material is a composite of a copolymer of ethylene and vinyl acetate, such as the Elvax™ resins commercially available from Ashland Chemical Company, and an elastomeric material such as thermoplastic rubber or vulcanized rubber. In some embodiments, the second material includes about 50 percent to about 80 percent by weight of the elastomeric material and about 20 percent to about 50 percent by weight of the copolymer of ethylene and vinyl acetate. In some embodiments, the copolymer can include vinyl acetate in the range of about 18 percent to about 28 percent by weight.

An illustrative but non-limiting example of a suitable second material is thermoplastic rubber marketed under the trademark KRATON™, which is marketed by GLS Plastics of 740B Industrial Drive, Cary, Ill. 60013. This thermoplastic rubber is unique in that it is injection moldable, FDA approved and readily adheres with copolymers of ethylene and vinyl acetate. Furthermore, the thermoplastic rubber has a melting or softening point significantly higher than that of EVA. Consequently, the elastomeric frame 400 is initially molded or formed after which the mouthguard base 300 may be injection molded therearound.

FIGS. 4 and 5 show the mouthguard base 300 molded about the elastomeric frame 400 with an optional tether mouth 470. The mouthguard base 300 is U-shaped and has an inner wall 310 and an outer wall 320 forming an upper channel 330 between the inner wall 310 and the outer wall 320 for receiving the jaw and teeth 12, 18, and 22 (see FIG. 1). The mouthguard base 300 has an anterior portion 340 and a posterior portion 342. In some embodiments, as illustrated, the material forming the mouthguard base 300 fills in and around the cushion pads 430, 432. In some embodiments, as illustrated, the cushion pads 430, 432 extend through the mouthguard base 300 and terminate at a lower surface 332 of the upper channel 330.

In some embodiments, the inner wall 310 and the outer wall 320 each have a uniform thickness as they extend upward from the upper channel 330. In some cases, this helps to minimize any tendency of the walls 310, 320 to sag together and bond during the fitting process. In some embodiments, the walls 310, 320 extend along the wall portion 460 of the elastomeric frame 400 and terminate along an upper edge thereof. In some embodiments, the outer wall 320 extends into the plurality of apertures 462 formed within the wall portion 460.

In some embodiments, the mouthguard base 300 is made of a first material of a softenable thermoplastic that can include one or more flavorants, including a flavorant that provides sweetness. The first material, in one embodiment, includes copolymers of ethylene and vinyl acetate, such as ethylene vinyl acetate (EVA). In another embodiment, the mouthguard base 300 is formed of a first material which is a copolymer having vinyl acetate in the range of 18% to 25% by weight. A commercial copolymer suitable for use is Elvax™ resin marketed by the GP Division of Ashland Chemical Co. In some embodiments, resins including Elvax™ Resin 350 through 450 have the desired proportions of vinyl acetate.

FIGS. 6, 7, and 8 show a mouthguard 200 having a liner 500 molded about the mouthguard base 300 and the elastomeric frame 400 with an optional tether mouth 470. The liner 500 is molded along the inner wall 310 and the outer wall 320 and extends across a bottom of the U-shaped channel 330, forming a receiving channel 510 that is adapted to engage the teeth of the upper jaw (FIG. 1). The receiving channel 510 includes an inner wall 520 and an outer wall 530. The liner 500, in one embodiment, has a constant thickness which is slightly thinner than the inner wall 310 and outer wall 320 of the mouthguard base 300. For example, the thickness of the liner 500 can be about 0.040 inches and the thickness of the walls 310, 320 can be about 0.060 inches.

The liner 500 is formed of a third material which softens at a temperature lower than the softening temperature of the first material and is softer than the first material when hardened. The third material can include one or more flavorants, including a flavorant that provides sweetness. In one embodiment, the third material is 100 percent of a copolymer of ethylene and vinyl acetate, and has at least 33 percent of vinyl acetate by weight. In yet another embodiment, the third material includes a copolymer of ethylene and vinyl acetate, and has at least 40 percent of vinyl acetate by weight. For example, a suitable third material is a soft EVA 40. Alternatively, another suitable third material includes EVA 100.

As discussed, the mouthguard base 300 includes a first material, the elastomeric frame 400 includes a second material and the liner 500 includes a third material. Each of the first material, the second material and the third material can independently include one or more flavorants, including a sweetener, a flavorant that provides sweetness such as sucralose. Each of the first material, the second material, and the third material can independently be free of flavorants.

In one embodiment, the first material, and hence the mouthguard base 300, can include a flavorant that provides sweetness. The second material, and hence the elastomeric frame 400, can include a flavorant providing a particular taste in order to help camouflage a "plastic smell" that could otherwise emanate or otherwise be tasted. The third material, and hence the liner 500, can include one or more flavorants.

As an illustrative but non-limiting example, a mouthguard formed of three different materials, such as the mouthguard 200, can have a first material can include a flavorant that provides an orange smell and/or taste. The mouthguard can have a second material that also includes a flavorant that provides an orange smell and/or taste. The mouthguard can have a third material that includes a flavorant that provides an orange smell and/or taste as well as a flavorant that provides sweetness. The orange flavor flavorants used in each of the first, second, and third materials can be the same flavorant, or can be complementary flavorants that provide different aspects of an "orange" taste. In some embodiments, the third material can include the flavorant providing sweetness, but not include any other flavorants contributing to the orange smell and/or taste.

It will be appreciated that the mouthguard 200 described herein is formed of three different polymers. In some embodiments, a mouthguard may only have two different materials. A first material can have a first flavorant while a second material has a second flavorant. One of the materials can include two or more flavorants while the other material is free of flavorants. In some embodiments, a mouthguard can be formed of four, five, or more different polymers, with flavorants selectively added to one or more of the different polymers. In some embodiments, a mouthguard can be formed of a single material such as silicone, EVA, or a formable thermoplastic material. The single material can include one or more flavorants, and in some cases can include a flavorant that provides sweetness.

To illustrate, a non-limiting example of a mouthguard is formed of two different materials having a first material including a flavorant that provides a strawberry smell and/or taste. The mouthguard also has a second material that also includes a flavorant that provides a strawberry smell and/or taste. The strawberry flavor flavorants used in each material can be the same flavorant or can be complementary flavorants that provide different aspects of a "strawberry" taste. In some embodiments, the second material can also include a flavorant that provides sweetness.

In some embodiments, one or more flavorants can be dispersed within one or more of the polymeric materials to provide the mouthguard 200 with a flavor that is reminiscent of a fruit punch flavor, a grape berry flavor, a mint flavor, an orange flavor, a bubblegum flavor, or a lemon flavor.

Figure 9:
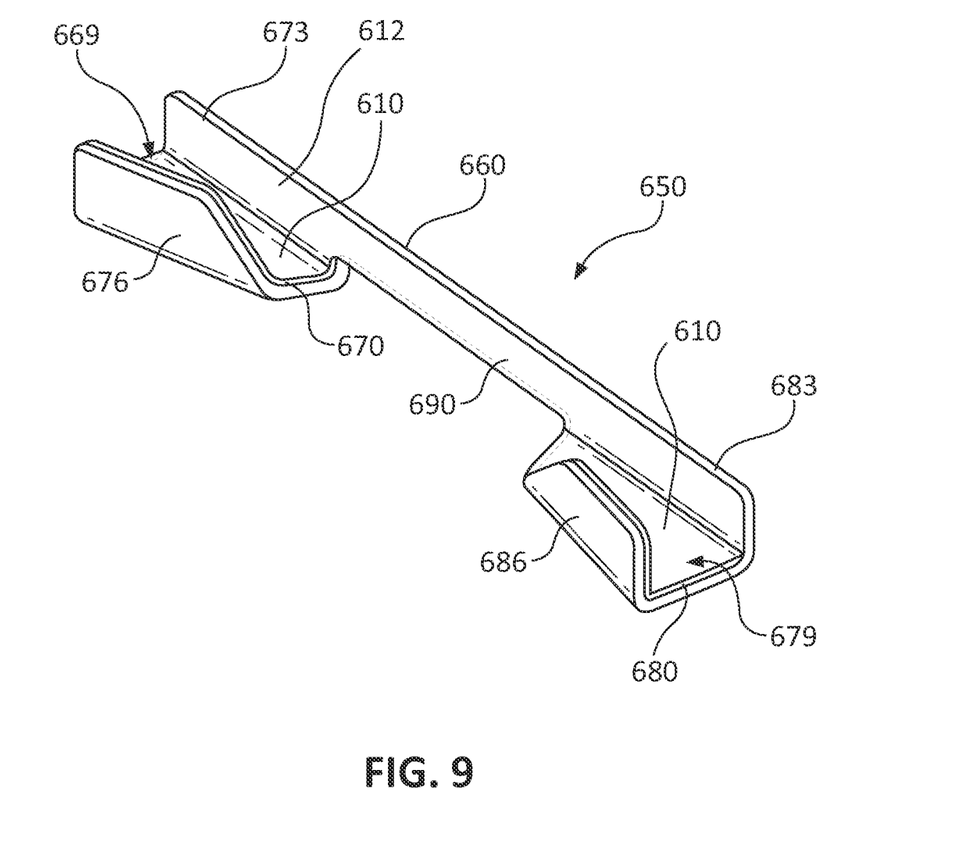
FIG. 9 is a raised perspective view of a mouthguard having a linear configuration, according to some embodiments.
Figure 10:
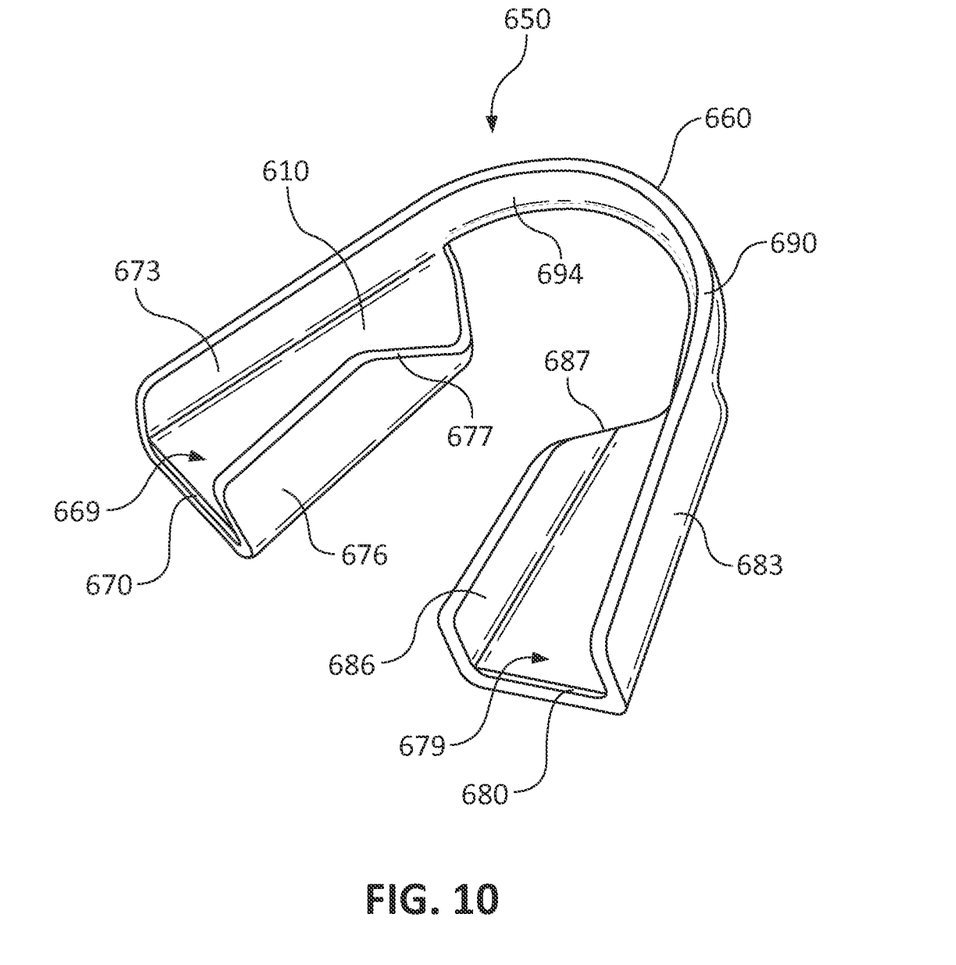
FIG. 10 is a raised perspective view of the mouthguard shown in FIG. 2 in a curved configuration, according to some embodiments.

In some embodiments, a mouthguard 650 as illustrated in the non-limiting views of FIGS. 9-10 has an initial linear or relaxed configuration as shown in FIG. 9 movable to a to a curved or stressed configuration and retain at least part of its curved configuration as shown in FIG. 10. The initial linear (relaxed) configuration feature is contrasted with the preformed U-shaped embodiments discussed above. In some embodiments, such an initial substantially linear configuration is resultant of a thermoplastic molding process, in which mouthguard 650 is molded from a resin into an initial, substantially linear configuration. In other embodiments, the "relaxed" configuration may be non-linear, with a central connection element 690 that is sufficiently flexible/resilient to be non-destructively manipulated into a substantially linear configuration. The central connection element 690 has a lower edge 694 optionally defining a general void that functions as a passageway for air to travel through while the mouthguard is gripped between the wearer's teeth. An exemplary mouthguard similar to mouthguard 650 can be found in the disclosure of Pub. No. US 2012/0085354, titled "MOUTHGUARD WITH LINEAR STORAGE CONFIGURATION," which is herein incorporated by reference in its entirety.

The mouthguard 650 includes a mouthguard body 660, a first end trough region 669, and a second end trough region 679 that is spaced apart from the first end trough region 669 and fixedly attached thereto by a central connection element 690. In use, the mouthguard 650 may be placed into a user's mouth so that at least some of the user's teeth rest within the first and second trough regions, 669 and 679 respectively, as defined by the teeth receiving trays, 670 and 680, exterior sidewalls, 673 and 683, and interior sidewalls, 676 and 686. Teeth receiving trays 670, 680 may be configured for cooperation with any desired number of teeth, and may be spaced apart by the central connection element 690 to a desired extent to engage with any set of teeth appropriate for a given application. In some embodiments, the first and second interior sidewalls, 676 and 686, each possess a cutaway section, 677 and 687 respectively. In some embodiments, the mouthguard body 660 or a component, such as the first end trough region 669, second end trough region 679, or central connection element 690, independently includes one or more flavorants or other additives.

In some embodiments, portions of the mouthguard that come into contact with biting areas of a wearer's teeth, such as liner 610, are softenable and formable while other portions of the mouthguard, such as a base layer 612, including an inner surface that comes into contact with outer surfaces of a wearer's teeth or the wearer's braces, is less softenable and formable. In some embodiments, the first and/or second trays 670, 680 may include upper and lower troughs or regions that are simultaneously cooperative with both maxillary and mandibular teeth, and may be fabricated from one or more materials providing a desired degree of flexibility. In some embodiments, the liner layer 610 is made of a material similar to that of liner 500. In some embodiments, the base layer 612 is made of a material similar to that of base 300 and/or elastomeric frame 400. Similar to embodiments described above, the liner layer 610 and/or the base layer 612 each independently includes one or more flavorants or other additives.

Figure 11:
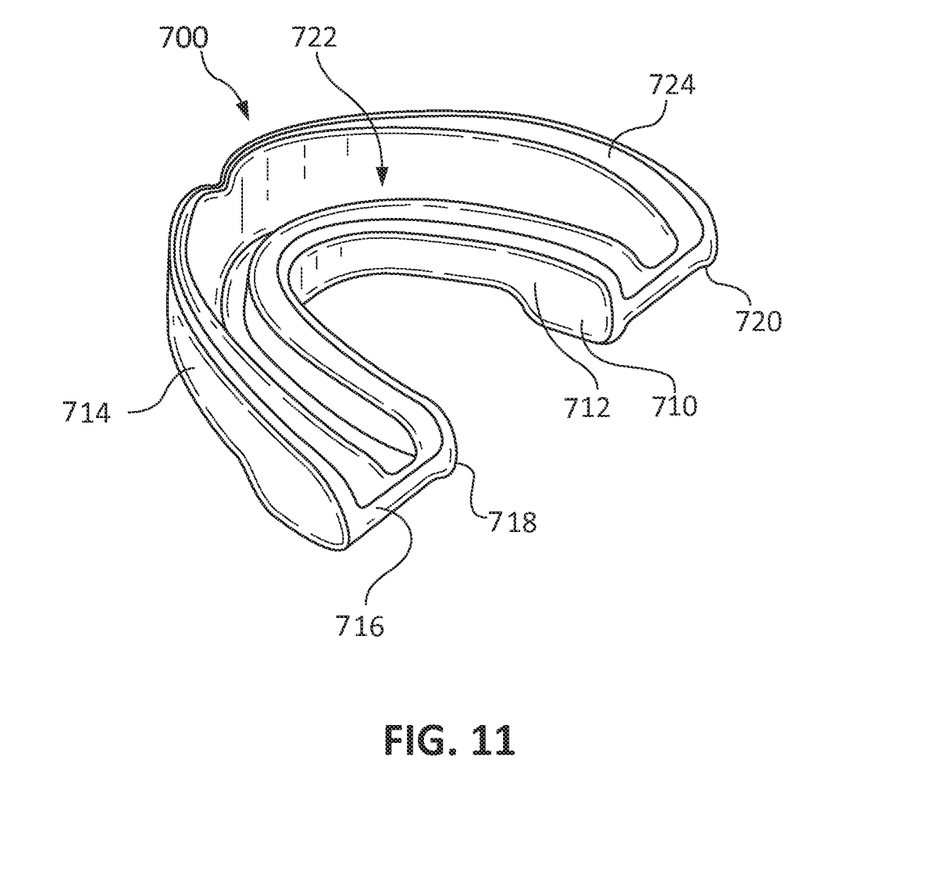
FIG. 11 is a raised perspective view of a mouthguard, according to some alternative embodiments.
Figure 12:
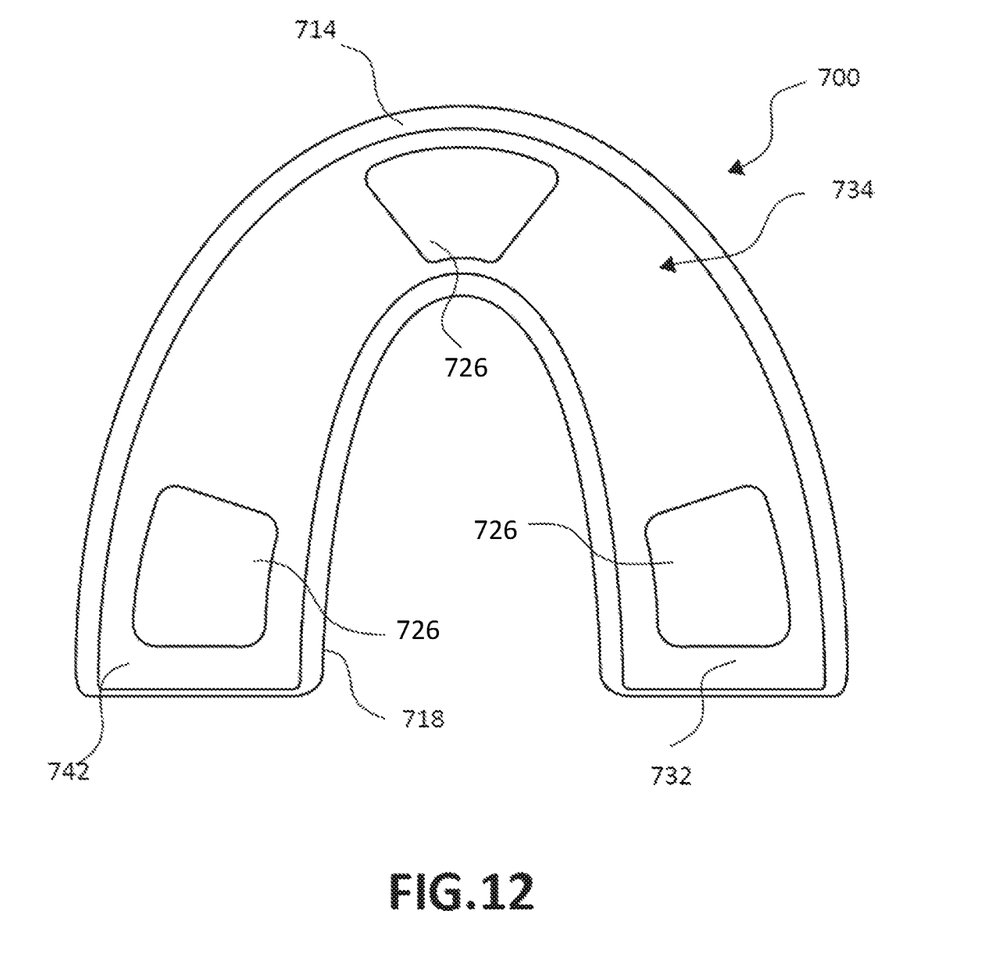
FIG. 12 is a bottom view of the mouthguard of FIG. 11, according to some alternative embodiments.

FIGS. 11 and 12 show non-limiting views of a mouthguard 700, according to some embodiments. As shown in the perspective view of FIG. 11, the mouthguard 700 includes a frame 710 having an upper inner wall 712, an upper outer wall 714, and an upper channel floor 716 extending between the upper inner wall 712 and the upper outer wall 714. In some embodiments, the frame 710 forms an upper channel 722 having a U-shaped cross-sectional profile. The upper channel floor 716 extends from a first end point 718 to a second end point 720. An upper moldable material 724 lines the upper channel 722 and provides the mouthguard 700 with the ability to be fitted to a wearer via a boil and bite process as noted above.

FIG. 12 shows the bottom view of the mouthguard 700 according to some embodiments. As shown, the mouthguard 700 has a lower channel floor 742, a lower outer wall 714, and a lower inner wall 718 defining a lower channel 732. A lower moldable material 726, similar to upper moldable material 724, is formed on the lower channel floor 742 to form a bite pad. In some embodiments, the lower moldable material 726 is an extension of upper moldable material 724 which has flowed through an opening in the channel floors 716 and 742. The lower channel floor 742 includes one or more lower open regions 734 where the lower moldable material 726 is not formed.

Similar to embodiments previously described, the mouthguard 700 includes two or more materials—for example, the frame 710 is formed of a first material and the moldable material 724 is formed of a second material, according to some embodiments. The first material can have a first flavorant while a second material has a second flavorant, for example. Although some embodiments include two materials, the mouthguard 700 can be formed of any number of layers with any number of materials having different flavorants, such as three, four, five, or more polymeric materials that are arranged in a corresponding number of layers and each including one or more different flavorants.

It is to be understood that the above description is intended to be illustrative, and not restrictive. Many other embodiments will be apparent to those of skill in the art upon reading and understanding the above description. For example, it is contemplated that features described in association with one embodiment are optionally employed in addition or as an alternative to features described in associate with another embodiment. The scope of the invention should, therefore, be determined with reference to the appended claims, along with the full scope of equivalents to which such claims are entitled.

The following is claimed:

1. A composite flavored mouthguard comprising:
   a mouthguard base having a generally U-shaped profile, the mouthguard base having an outer wall and an inner wall, the outer wall and inner wall forming an upper channel, the mouthguard base formed entirely of a first material;
   an elastomeric frame including an impact shield disposed over the outer wall, a first cushion pad and a second cushion pad positioned between the outer wall and inner wall of the mouthguard base, the elastomeric frame formed entirely of a second material, wherein the shield, the outer wall, the inner wall, and the first and second cushion pads define a bottom surface of the mouthguard; and
   a liner disposed within the upper channel and defining a top surface of the mouthguard, the liner formed entirely of a third material,
   wherein at least one of the first material, the second material, or the third material is unsweetened and includes an unsweetened flavorant, and at least one other of the first material, the second material, or the third material includes a sweetener consisting essentially of sugar alcohols, natural sugars, artificial sugars, and combinations thereof.

2. The composite flavored mouthguard of claim 1, wherein the third material includes a flavorant consisting essentially of sugar alcohols, natural sugars, artificial sugars, and combinations thereof.

3. The composite flavored mouthguard of claim 2, wherein the first material and the second material are each unsweetened and include a flavorant.

4. The composite flavored mouthguard of claim 2, wherein either the first material or the second material is unsweetened and includes a flavorant.

5. The composite flavored mouthguard of claim 1, wherein the third material includes at least two flavorants, with one of the flavorants consisting essentially of sugar alcohols, natural and artificial sugars, and combinations thereof.

6. The composite flavored mouthguard of claim 5, wherein the first material and the second material are each unsweetened and include a flavorant.

7. The composite flavored mouthguard of claim 5, wherein the first material includes at least two flavorants, with one of the flavorants providing sweetness, and the second material includes flavorant.

8. The composite flavored mouthguard of claim 1, wherein the third material includes only one flavorant providing sweetness.

9. The composite flavored mouthguard of claim 8, wherein the first material or the second material includes only one flavorant providing sweetness.

10. The composite flavored mouthguard of claim 1, wherein the first material includes at least two flavorants, with one of the flavorants providing sweetness.

11. The composite flavored mouthguard of claim 1, wherein the second material includes at least two flavorants, with one of the flavorants providing sweetness.

12. The composite flavored mouthguard of claim 1, wherein the first material includes a copolymer of ethylene and vinyl acetate having about 18 to about 25 weight percent vinyl acetate within the copolymer.

13. The composite flavored mouthguard of claim 1, wherein the second material includes an injection moldable thermoplastic rubber.

14. The composite flavored mouthguard of claim 1, wherein the second material includes a composite of a copolymer of ethylene and vinyl acetate and a rubber.

15. The composite flavored mouthguard of claim 1, wherein the third material includes a copolymer of ethylene and vinyl acetate having at least about 33 weight percent vinyl acetate within the copolymer.

16. The composite flavored mouthguard of claim 1, wherein the first and second cushion pads extend from the bottom surface of the mouthguard through the mouthguard base to the liner.

17. The composite flavored mouthguard of claim 1, wherein the remaining one of the first material, second material, or third material is free of sweeteners and flavorants.

18. A composite flavored mouthguard comprising:
an elastomeric frame formed entirely of a first material and having a shield, a first cushion pad, and a second cushion pad;
a base having an outer wall positioned between the shield and the first and second cushion pads, and an inner wall positioned behind the first and second cushion pads, the base forming an upper channel configured to receive the teeth of an upper jaw of a user when worn and formed entirely of a second material, wherein the outer wall, the inner wall, and the first and second cushion pads define a bottom surface of the mouthguard; and
a liner disposed within the upper channel and defining an upper surface of the mouthguard, the liner formed entirely of a third material,
wherein at least one of the first material, second material, and third material is unsweetened and includes an unsweetened flavorant that lacks any sugar alcohol, natural sugar, and artificial sugar sweetener and at least one other of the first material, second, and third material includes a sweetener consisting essentially of at least one of sorbitol, maltitol, xylitol, mannitol, erythritol, lactitol, saccharin, sucralose, extracts from the Stevia plant, and combinations thereof.

19. The composite flavored mouthguard of claim 18, further including a second flavorant in the other of the first material and second material, the first flavorant providing a first taste component and the second flavorant provides a second taste component that is different from the first taste component.

20. The composite flavored mouthguard of claim 18, wherein the elastomeric frame forms a lower channel opposite the upper channel, the liner flows through at least one opening in the elastomeric frame to the lower channel to form a bite pad.

21. A composite flavored mouthguard comprising:
a mouthguard base having an outer wall and an inner wall, the outer wall and inner wall defining a channel having a U-shaped profile and configured to receive the teeth of the upper jaw of a user when worn, the mouthguard base formed entirely of a first material including an unsweetened flavorant that lacks any sugar alcohol, natural sugar, and artificial sugar sweetener;
a frame including a shield positioned around the outer-wall, and first and second cushion pads positioned between the outer wall and inner wall along a bottom surface of the mouthguard, the frame formed entirely of a second material; and
a liner disposed within the channel and defining a top surface of the mouthguard, the liner formed of a third material including a sweetener consisting essentially of at least one of sorbitol, maltitol, xylitol, mannitol, erythritol, lactitol, saccharin, sucralose, extracts from the Stevia plant, and combinations thereof,
wherein the unsweetened flavorant provides an unsweetened, first taste component and the sweetener provides a second, sweet taste component that is different from the first, unsweetened taste component.

22. The composite flavored mouthguard of claim 21, wherein the first taste component comprises a fruit punch flavor, a grape berry flavor, a mint flavor, an orange flavor, a bubblegum flavor, or a lemon flavor.

23. A composite flavored mouthguard having U-shaped cross-section defined by a first vertical wall, a second vertical wall and a horizontal wall extending between the first and second vertical walls, the first vertical wall defining an inward surface of the mouthguard configured to face inwardly into a mouth of a wearer, the second vertical wall defining an outward surface of the mouthguard configured to face outwardly away from the mouth of the wearer, and the horizontal wall defining an upward surface configured to face toward an upper set of teeth of the wearer and a downward surface configured to face away from the upper set of teeth of the wearer, the mouthguard comprising:
a first layer defining the outward surface of the mouthguard; and
a second layer defining the inward surface of the mouthguard;
wherein at least one of the first layer and the second layer is unsweetened and includes an unsweetened flavorant, and at least one other of the first layer and the second layer is sweetened and includes a sweetener consisting essentially of sugar alcohols, natural sugars, artificial sugars, and combinations thereof such that the mouthguard is configured to deliver the unsweetened flavorant to a first location within the mouth and the sweetener to a second location within the mouth that is different from the first location within the mouth.

* * * * *